United States Patent [19]

Karrer

[11] Patent Number: 4,788,283

[45] Date of Patent: Nov. 29, 1988

[54] 1-DIORGANOCARBAMOYL-POLYALKYL-PIPERIDINES

[75] Inventor: Friedrich Karrer, Zofingen, Switzerland

[73] Assignee: Ciba-Geigy Corporation, Ardsley, N.Y.

[21] Appl. No.: 842,610

[22] Filed: Mar. 21, 1986

Related U.S. Application Data

[62] Division of Ser. No. 490,288, May 2, 1983, Pat. No. 4,590,268.

[30] Foreign Application Priority Data

May 10, 1982 [CH] Switzerland .................. 2890/82

[51] Int. Cl.$^4$ ............................ C07D 211/16
[52] U.S. Cl. .................... 544/82; 546/186; 546/187
[58] Field of Search ............ 544/121, 212, 218, 230; 546/15, 186, 187, 188, 189, 192, 207; 549/82

[56] References Cited

U.S. PATENT DOCUMENTS

| | | | |
|---|---|---|---|
| 4,021,432 | 5/1977 | Holt et al. | 524/103 |
| 4,069,196 | 1/1978 | Ramey et al. | 260/45.8 N |
| 4,344,876 | 8/1982 | Berner | 524/91 |
| 4,369,321 | 1/1983 | Cantatore | 546/18.7 |
| 4,412,021 | 10/1983 | Karrer | 524/102 |
| 4,556,714 | 12/1985 | Karrer | 546/189 |
| 4,569,997 | 2/1986 | Karrer | 546/189 |
| 4,590,268 | 5/1986 | Karrer | 546/189 |

FOREIGN PATENT DOCUMENTS 2351102 9/1977 France .
367171 2/1963 Switzerland .

OTHER PUBLICATIONS

Journal F. Prakt. Chemie 319, 516–521 (1977).

Primary Examiner—Kriellion Morgan
Attorney, Agent, or Firm—Harry Falber

[57] ABSTRACT

Compounds containing a group of the formula I

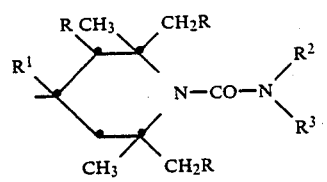

in which R is H or $C_1$–$C_4$-alkyl, $R^1$ is H, CN, an acyloxy group or a free valency and $R^2$ and $R^3$ are organic radicals can be prepared in a simple manner from the corresponding compounds containing a group of the formula Ia

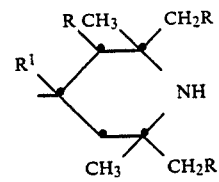

by stepwise reaction with phosgene and a secondary amine $R^2$—NH—$R^3$ in the presence of a molar amount of a base. The N-diorganocarbamoyl compounds containing the group I are outstanding light stabilizers, in particular for organic polymers. They can be converted by secondary reactions into other compounds which contain the group I and which are not accessible by direct phosgenation. Many of the products thus obtainable by phosgenation or conversion are novel compounds.

1 Claim, No Drawings

1-DIORGANOCARBAMOYL-POLYALKYLPIPERIDINES

This is a divisional of application Ser. No. 490,288, filed on May 2, 1983, now U.S. Pat. No. 4,590,268.

The invention relates to a process for the preparation of polyalkylpiperidine derivatives which are substituted in the 1-position by a diorganocarbamoyl group, and to novel compounds from this group of polyalkylpiperidine derivatives.

It has been disclosed that sterically hindered polyalkylpiperidine derivatives are excellent light stabilisers for organic materials, in particular for organic polymers. It is important here that the piperidine ring is alkylated in the 2- and 6-positions, whilst the nitrogen in the 1-position can be unsubstituted or substituted by various organic grpoups. German Offenlegungsschrift No. 2,258,752 has already proposed the use of polyalkylpiperidine derivatives which have, on the nitrogen of the piperidine ring, a carbamoyl group —CO—$NH_2$ or a monosubstituted or disubstituted carbamoyl group —CO—NHR or —CO—$NR_2$, in which R is an organic radical. Those compounds containing the carbamoyl radical —CO—NHR can be prepared from the NH-piperidines by reaction with isocyanates, and German Offenlegungsschrift No. 2,258,752 has disclosed a number of specific compounds of this type. However, this Offenlegungsschrift mentioned compounds having a disubstituted carbamoyl group —CO—$NR_2$ on the piperidine nitrogen only in general terms, and recommended reaction of the corresponding NH-piperidines with a carbamoyl chloride Cl-CO-$NR_2$ or with a carbamic acid ester RO—CO—$NR_2$ as a general method of preparation. If attempts are made to use either of these methods for the preparation of 1-diorganocarbamoyl-polyalkylpiperidines, difficulties are encountered. No reaction takes place at room temperature or slightly elevated temperature, and at higher temperatures dark-coloured reaction products are obtained, from which only a low yield of the desired products are obtained by the conventional methods of purification. However, since the resulting N-disubstituted 1-carbamoylpiperidines have proved to be superior stabilisers to the monosubstituted analogues, there was a considerable interst in discovering an industrially usable preparation process for these compounds.

Furthermore, S. S. Berg and D. F. Cowling (J. Chem. Soc. (C) 1971, 1653–8) have described the reaction of 2,2,6,6-tetramethylpiperidine with phosgene in the molar ratio of 2:1. The result was however not the formation of the desired urea but the cleavage of the piperidine ring, whereby a mixture of isomeric noncyclic isocyanates was formed.

It has been found that, surprisingly, sterically hindered polyalkylpiperidines which are unsubstituted in the 1-position can readily be reacted with phosgene at only low temperatures, and that the 1-chlorocarbonyl compounds thus obtained can just as readily be further reacted with secondary amines to give the corresponding 1-diorganocarbamoyl compounds. The chlorocarbonyl compounds can be reacted with the secondary amine without being isolated, i.e. the two reaction stages can be carried out as a one-pot reaction. The preparation of unsymmetrical tetra-substituted ureas from a secondary amine A by stepwise reaction with phosgene and a secondary amine B is known per se, and it is also known that such a reaction is carried out in an inert solvent and in the presence of a stoichiometric amount of an HCl-bonding base. However, it was not to be expected that this reaction can be applied to the sterically hindered 2,2,6,6-tetraalkylpiperidines under such mild conditions, since it is known that acylation of such piperidines with carboxylic acid chlorides proceeds only at elevated temperature and even then only relatively slowly.

The invention thus relates to a process for the preparation of compounds containing a group of the formula I

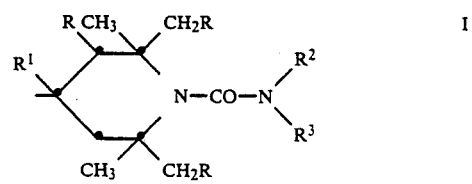

in which R is hydrogen or $C_1$–$C_4$-alkyl, $R^1$ is hydrogen, $C_1$–$C_{12}$-alkoxy, $C_2$–$C_{20}$-alkanoyloxy, benzoyloxy, $C_3$–$C_{25}$-carbamoyloxy, CN or a free valency, $R^2$ is $C_1$–$C_{18}$-alkyl, $C_3$–$C_{12}$-alkoxyalkyl, $C_2$–$C_8$-hydroxyalkyl, $C_3$–$C_{12}$-alkenyl $C_7$–$C_{14}$-aralkyl, $C_6$–$C_{14}$-aryl, $C_7$–$C_{14}$-alkaryl, $C_3$–$C_7$-cycloalkyl or 2,2,6,6-tetramethylpiperidin-4-yl and $R^3$ has one of the meanings of $R^2$, or $R^2$ and $R^3$, together with the N atom to which they are bonded, form a 5- to 7-membered heterocyclic ring, and in which the free valency (valencies) is(are) bonded to hydrogen, oxo-oxygen or any low-molecular or high-molecular organic radical, by reacting a compound containing a group of the formula Ia

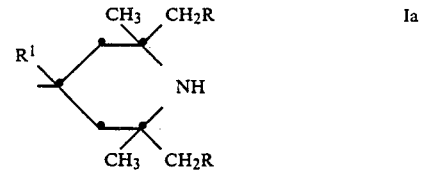

with phosgene in an inert solvent in the presence of a molar amount of a base, and subsequently reacting the product with a secondary amine of the formula $R^2$—NH—$R^3$, also in the presence of a molar amount of a base.

An alkyl radical R in formula I or Ia can be, for example, methyl, ethyl, propyl or butyl. R is preferably hydrogen.

An alkoxy radical $R^1$ can be, for example, methoxy, ethoxy, isopropoxy, butoxy, hexyloxy, octyloxy or dodecyloxy. Preferred alkoxy radicals are $C_1$–$C_4$-alkoxy radicals.

An alkanoyloxy radical $R^1$ can be, for example, acetoxy, propionoxy, hexanoyloxy or stearoyloxy. A carbamoyloxy radical $R^1$ can be monosubstituted or disubstituted carbamoyloxy, for example methylcarbamoyloxy, phenylcarbamoyloxy, dimethylcarbamoyloxy, dibutylcarbamoyloxy or di(dodecyl)carbamoyloxy.

$R^1$ is preferably hydrogen or a free valency.

An alkyl radical $R^2$ or $R^3$ is, for example, methyl, ethyl, propyl, isopropyl, butyl, sec.butyl, isoamyl, hexyl, n-octyl, 2-ethylhexyl, 1,1,3,3-tetramethylbutyl, decyl, undecyl, dodecyl, hexadecyl or octadecyl. An alkoxyalkyl or hydroxyalkyl radical $R^2$ or $R^3$ is, for example, 2-methoxyethyl, 2-ethoxyethyl, 2-butoxyethyl, 2-isopropoxyethyl, 3-butoxypropyl, 2-octyloxypropyl, 2-hydroxyethyl, 2-hydroxypropyl or 2-hydroxybutyl. An alkenyl radical $R^2$ or $R^3$ is, for example, allyl, methallyl or 2-butenyl. An aralkyl radical $R^2$ or $R^3$ can be, for example, benzyl, 2-phenethyl, 3-phenylpropyl or 1,1-dimethylbenzyl. An aryl or alkaryl radical $R^2$ or $R^3$ can be, for example, phenyl, naphthyl, tolyl, xylyl, 4-tert.-butylphenyl or 4-octylphenyl. A cycloalkyl radical $R^2$ or $R^3$ can be, for example, cyclopropyl, cyclopentyl, cyclohexyl or methylcyclohexyl. If $R^2$ and $R^3$, together with the N atom to which they are bonded, from a heterocyclic ring, this can be, for example, a piperidine, pyrrolidine, morpholine, or 4-alkylpiperidine ring.

The compounds containing a group I can be monomeric, oligomeric or polymeric compounds. Monomeric compounds can be represented by the general formula II

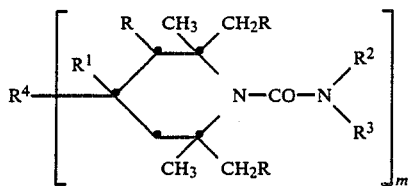

in which m is an integer from 1 to 4, $R^1$ is hydrogen, $C_2$–$C_{12}$-alkoxy, $C_2$–$C_{20}$-alkanoyloxy, benzoyloxy, $C_3$–$C_{25}$-carbamoyloxy or CN and $R^4$ is hydrogen or an m-valent organic radical, or $R^1$ and $R^4$ together are oxo-oxygen or a divalent organic radical, and R, $R^2$ and $R^3$ are as defined above.

Oligomeric or polymeric compounds are those in which several groups of the formula I are bonded directly or via an intermediate member to an oligomer or polymer.

The following classes of compounds which can be prepared according to the invention are of particular importance.

(a) Compounds of the formula III

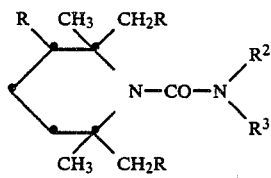

in which R, $R^2$ and $R^3$ are as defined above.

(b) Compounds of the formula IV

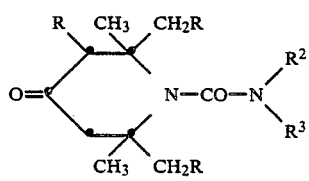

in which R, $R^2$ and $R^3$ are as defined above.

(c) Compounds of the formula V

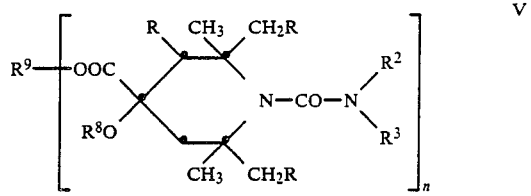

in which n is a number from 1 to 4, $R^8$ is $C_1$–$C_4$-alkyl or $C_2$–$C_{12}$-alkanoyl, $R^9$ is the n-valent radical of a $C_1$–$C_{20}$-alcohol, $C_2$–$C_{16}$-diol, $C_3$–$C_{18}$-triol or $C_4$–$C_{20}$-tetrol, which can be interrupted by one or more oxygen atoms, and R, $R^2$ and $R^3$ are as defined above.

An alcohol radical $R^9$ is, for example, the monovalent radical of methanol, ethanol, isopropanol, tert.-butanol, isopentanol, 2-methoxyethanol, n-hexanol, cyclohexanol 2-ethylhexanol, 2-ethylhexanol, isooctanol, cyclooctanol, n-decanol, benzyl alcohol, n-dodecanol or n-octadecanol, the divalent radical of ethylene glycol, propane-1,2-diol, butane-1,4-diol hexane-1,6-diol, 2,2,4-trimethylhexane-1,6-diol, dodecane-1,12-diol, xylylene glycol, 1,4-di(hydroxymethyl)cyclohexane, diethylene glycol or triethylene glycol, the trivalent radical of glycerol, trimethylolethane or trimethylolpropane or the tetravalent radical of pentaerythritol, these radicals being formed by detaching n hydroxyl groups from the n-hydric alcohols.

(d) Compounds of the formula VI

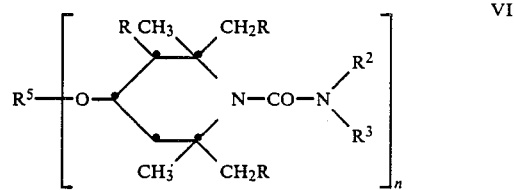

in which n is an integer from 1 to 4, and, if n is 1, $R^5$ is $C_1$–$C_{18}$-alkyl, which can be interrupted by one or more oxygen atoms, or is cyanoethyl, benzyl, glycidyl or a monovalent acyl radical of an aliphatic, cycloaliphatic, araliphatic, aromatic or heterocyclic carboxylic acid, aminocarboxylic acid, carbamic acid or phosphorus-containing acid, or, if n is 2, $R^5$ is $C_2C_{12}$-alkylene, $C_4$–$C_{12}$-alkenylene, xylylene or a divalent acyl radical of an aliphatic, cycloaliphatic, araliphatic, aromatic or heterocyclic dicarboxylic acid, dicarbamic acid or phosphorus-containing acid, or, if n is 3, $R^5$ is a trivalent acyl radical of an aliphatic, cycloaliphatic, araliphatic, aromatic or heterocylic tricarboxylic acid, tricarbamic acid or phosphorus-containing acid, or, if n is 4, $R^5$ is tetravalent acyl radical of an aliphatic, cycloaliphatic or aromatic tetracarboxylic acid, and R, $R^2$ and $R^3$ are as defined in claim 1.

Preferred compounds of the formula VI are those in which n is 1 or 2 and, if n is 1, $R^5$ is the monovalent acyl radical of an aliphatic carboxylic acid having 2 to 18 C atoms, a cycloaliphatic carboxylic acid having 5 to 12 C atoms or an aromatic carboxylic acid having 7 to 15 C atoms, or, if n is 2, $R^5$ is the divalent acyl radical of an aliphatic dicarboxylic acid having 2 to 36 C atoms, a cycloaliphatic or aromatic dicarboxylic acid having 8 to 16 C atoms or a cycloaliphatic or aromatic dicarbamic acid having 6 to 16 C atoms.

An alkyl radical $R^5$ can be, for example, methyl, ethyl, propyl, n-butyl, sec.-butyl, tert.-butyl, n-hexyl, n-octyl, 2-ethylhexyl, n-decyl, n-dodecyl or n-octadecyl. An alkylene radical $R^5$ can be, for example, 1,2-ethylene, 1,4-butylene, 1,8-octylene or 1,2-dodecylene. An alkenylene radical $R^5$ can be, for example, 2-buten-1,4-ylene.

A monovalent acyl radical $R^5$ can be, for example, the radical of acetic, propionic, butyric, isovaleric, acrylic, methacrylic, caproic, caprylic, lauric, palmitic, oleic, stearic, benzoic, 4-chlorobenzoic, 4-octylbenzoic, toluic, phenoxyacetic, salicylic, 2-phenylpropionic, cyclohexanecarboxylic, furan-2-carboxylic, dimethylcarbamic, diphenylcarbamic, cyclohexylcarbamic or diphenylphosphinic acid.

A divalent acyl radical $R^5$ can be, for example, the radical of oxalic, malonic, succinic, glutaric, diethylmalonic, dodecylsuccinic, dibenzylmalonic, adipic, sebacic, maleic, fumaric, diglycolic, isophthalic, terephthalic, diphenyl-4,4′-dicarboxylic, tetrahydrophthalic, hexahydroterephthalic, decahydronaphthalene-1,4-dicarboxylic, hexamethylenedicarbamic, toluylene-2,4-dicarbamic or phenylphosphonic acid.

A trivalent or tetravalent acyl radical $R^5$ is, for example, the radical of tricarballylic, trimellitic, nitrilotriacetic, phosphoric, phosphorous, pyromellitic, cyclohexanone-2,2,6,6-tetracarboxylic or 4,4′-methylenediphthalic acid.

$R^5$ can also be acyl radical of a dicarboxylic or tricarboxylic acid such as is prepared industrially by dimerisation or trimerisation of unsaturated fatty acids, for example linoleic acid, or by Diels-Alder addition of acrylic acid onto linoleic acid.

(e) Compounds of the formula VII

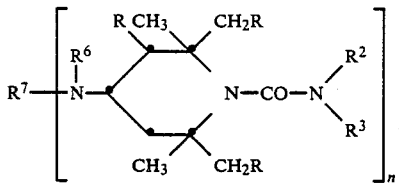

in which n is 1 or 2, $R^6$ is $C_1$–$C_{12}$-alkyl, $C_3$–$C_{12}$-alkoxyalkyl, $C_5$–$C_8$-cycloalkyl, $C_7$–$C_9$-aralkyl, $C_2$–$C_{18}$-alkanoyl, $C_3$–$C_5$-alkenoyl, benzoyl, $C_2$–$C_{13}$-alkoxycarbonyl, $C_7$–$C_{11}$-aryloxycarbonyl or a group of the formula

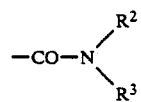

and, if n is 1, $R^7$ is $C_1$–$C_{12}$-alkyl, $C_3$–$C_{12}$-alkoxyalkyl, $C_5$–$C_8$-cycloalkyl, $C_3$–$C_8$-alkenyl or cyanoethyl or, if $R^6$ is alkanoyl, alkenoyl, benzoyl, alkoxycarbonyl, aryloxycarbonyl or carbamoyl, $R^7$ can also be hydrogen, or, if n is 2, $R^7$ is $C_2$–$C_{12}$-alkylene, $C_6$–$C_{15}$-arylene or xylylene, or if $R^6$ is alkyl, cycloalkyl or aralkyl, $R^7$ can also be a divalent acyl radical of an aliphatic, cycloaliphatic or aromatic dicarboxylic acid or dicarbamic acid, or, if n is 1, $R^6$ and $R^7$, together with the N atom, are an imide radical of an aliphatic, cycloaliphatic or aromatic 1,2-dicarboxylic acid having 4 to 12 C atoms.

An alkyl radical $R^6$ or $R^7$ can be, for example, methyl, ethyl, isopropyl, n-butyl, tert.-butyl, isoamyl, n-hexyl, n-octyl, 2-ethylhexyl, n-decyl or n-dodecyl. An alkenyl radical $R^7$ can be, for example, allyl, methallyl, but-2-en-1-yl or 1-dimethylallyl. A cycloalkyl radical $R^6$ or $R^7$ can be, for example, cyclopentyl, cyclohexyl, cycloheptyl or cyclooctyl.

An aralkyl radical $R^6$ can be, for example, benzyl, phenethyl or phenylpropyl. An acyl radical $R^6$ can be, for example, acetyl, propionyl, butyroyl, hexanoyl, octanoyl, lauroyl, palmitoyl, stearoyl, acryloyl, methacryloyl, benzoyl, ethoxycarbonyl, butoxycarbonyl, dodecyloxycarbonyl, phenoxycarbonyl or tolyloxycarbonyl.

An alkylene radical $R^7$ can be, for example, 1,2-ethylene, 1,3-propylene or tetra-, hexa-, octa- or dodecamethylene. An arylene radical $R^7$ can be, for example, phenylene, tolylene, diphenylene, diphenylenemethane or diphenylene-2,2-propane. A divalent acyl radical $R^7$ can be, for example, oxalyl, succinoyl, adipoyl, sebacoyl, cyclohexanedicarbonyl, teraphthaloyl or hexamethylenedicarbamoyl.

If n is 1, $R^6$ and $R^7$, together with the N atom, can be a cyclic imide radical, for example a succinimide, maleimide, phthalimide or hexahydrophthalimide radical.

(f) Compounds of the formula VIII

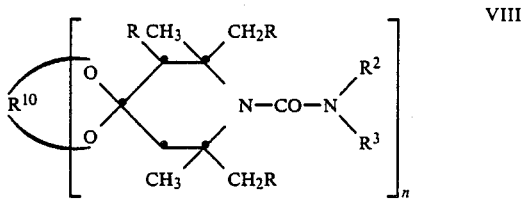

in which n is 1 or 2, and, if n is 1, $R^{10}$ is $C_2$–$C_8$-alkylene or $C_4$–$C_{22}$-acyloxyalkylene, or, if n is 2, $R^{10}$ is the group $(-CH_2)_2C(CH_2-)_2$, and R, $R^2$ and $R^3$ are as defined above.

In this formula, $R^{10}$ can be, for example, 1,2-ethylene, 1,2-propylene, 1,3-propylene, 2,2-dimethyl-1,3-propylene, 1,2-octylene, 2-(acetoxymethyl)-2-ethyl-1,3-propylene, 2-(lauroyloxymethyl)-2-ethyl-1,3-propylene, 2-(butyroyloxymethyl)-2-methyl-1,3-propylene or 2-acetoxy-1,3-propylene.

(g) Compounds of the formula IX, X or XI

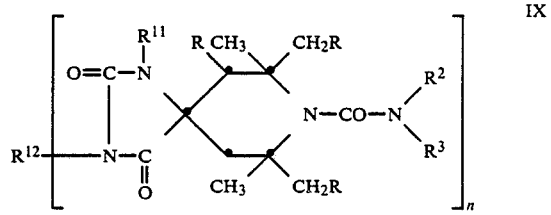

in which n is 1 or 2, $R^{11}$ is hydrogen, $C_1$–$C_{12}$-alkyl, allyl, benzyl, glycidyl or $C_2$–$C_6$-alkoxyalkyl, and, if n is 1, $R^{12}$ is hydrogen, $C_1$–$C_{12}$-alkyl, $C_3$–$C_5$-alkenyl, $C_7$–$C_9$-aralkyl, $C_5$–$C_8$-cycloalkyl, $C_2$–$C_4$-hydroxyalkyl, $C_3$–$C_6$-alkoxyalkyl, $C_6$–$C_{10}$-aryl or glycidyl, or, if n is 2, $R^{12}$ is $C_2$–$C_{12}$-alkylene, $C_6$–$C_{15}$-arylene or $C_4$–$C_8$-alkenylene, and R, $R^2$ and $R^3$ are as defined above. are H, $C_1$–$C_{12}$-alkyl, $C_7$–$C_9$-aralkyl, or $C_6$–$C_{10}$-aryl which is unsubstituted or substituted by halogen or $C_1$–$C_4$-alkyl, or $R^{13}$ and $R^{14}$ together are $C_4$–$C_{11}$-alkylene, and, if n is 1, $R^{15}$ is hydrogen, $C_1$–$C_{12}$-alkyl, $C_3$–$C_5$-alkenyl, $C_7$–$C_9$-aralkyl, $C_5$–$C_8$-cycloalkyl, glycidyl, $C_2$–$C_{18}$-alkanoyl, $C_3$–$C_5$-alkenoyl, benzoyl or toluyl, or, if n is 2, $R^{15}$ is $C_2$–$C_{12}$-alkylene, $C_4$–$C_8$-alkenylene or $C_8$–$C_{14}$-arylenedialkylene, and R, $R^2$ and $R^3$ are as defined above.

In these formulae, $R^{11}$ and $R^{12}$ can be straight-chain or branched alkyl, for example methyl, ethyl, isopropyl, n-butyl, sec.-butyl, tert.-butyl, n-hexyl, n-octyl, 2-ethylhexyl, n-decyl or n-dodecyl. An alkenyl radical $R^{12}$ can be, for example, allyl, methallyl or 1,1-dimethylallyl. An alkoxyalkyl radical $R^{11}$ can be, for example, 2-methoxyethyl, 2-butoxyethyl or 3-ethoxypropyl. A hydroxyalkyl or alkoxyalkyl radical $R^{12}$ can be, for example, 2-hydroxyethyl, 2-hydroxypropyl or 2-ethoxyethyl. An aralkyl radical $R^{12}$ can be, for example, benzyl, 2-phenethyl or 1,1-dimethylbenzyl. A cycloalkyl radical $R^{12}$ can be for example, cyclopentyl, cyclohexyl, cycloheptyl or cyclooctyl.

An alkylene radical $R^{12}$ can be, for example 1,2-ethylene, 1,3-propylene or tetra-, hexa-, octa-, deca- or dodeca-methylene. An alkenylene radical $R^{12}$ can be, for example, but-2-en-1,4-ylene or hex-3-en-1,6-ylene. An arylene radical $R^{12}$ can be, for example, phenylene, naphthylene, diphenylene or 2,2-diphenylenepropane.

(h) Compounds of the formula XII

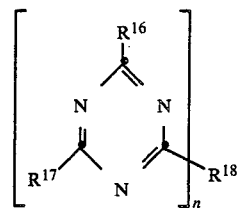

XII in which n is 1 or 2, $R^{16}$ is a group of the formula

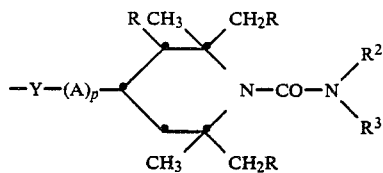

in which R, $R^2$ and $R^3$ are as defined in claim 1, Y is —O— or —$NR^{19}$—, $R^{19}$ is H, $C_1$–$C_{12}$-alkyl, $C_3$–$C_6$-alkoxyalkyl, cyclohexyl, benzyl or a group

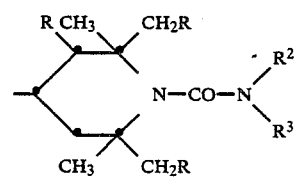

A is $C_2$–$C_6$-alkylene or —$(CH_2)_3$—O— and p is zero or 1, and $R^{17}$ has one of the meanings given for $R^{16}$, or is —$NR^{20}R^{21}$, —$OR^{22}$, —$NHCH_2OR^{23}$ or —$N(CH_2OR^{23})_2$, in which $R^{20}$ has one of the meanings given for $R^{19}$ and $R^{21}$ is $C_1$–$C_{12}$-alkyl, cyclohexyl or benzyl, or $R^{20}$ and $R^{21}$ together are $C_4$–$C_5$-alkylene or oxaalkylene, $R^{22}$ is $C_1$–$C_{12}$-alkyl or phenyl and $R^{23}$ is $C^1$–$C^4$-alkyl, and, if n is 1, $R^{18}$ has one of the meanings given for $R^{16}$ and $R^{17}$, or, if n is 2, $R^{18}$ is a group —Y—Q—Y—, in which Q is $C_2$–$C_{12}$-alkylene, $C_4$–$C_{12}$-alkylene which is interrupted by —O—, —NH—, —N-alkyl or by a group of the formula

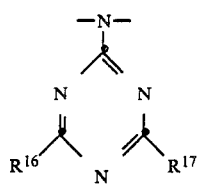

or Q is cyclohexylene, xylylene or phenylene.

In these formulae, $R^{19}$, $R^{21}$ and $R^{22}$ can be straight-chain or branched alkyl, for example methyl, ethyl, isopropyl, tert.-butyl, isoamyl, n-hexyl, 2-ethylhexyl, isononyl, n-decyl or n-dodecyl. An alkoxyalkyl radical $R^{19}$ can be, for example, 2-methoxyethyl, 2-butoxyethyl or 2-ethoxybutyl.

An alkylene radical A or Q can be straight-chain or branched, for example 1,2-ethylene, 1,3-propylene, 1,2-butylene or 1,2-hexylene. Q can moreover also be, for example, hexa-, octa-, deca-, dodeca- or 2,4,4-trimethylhexamethylene. An interrupted alkylene radical Q can be, for example, 3-oxapent-1,5-ylene, 3,6-dioxaoct-1,8-ylene, 3-azapent-1,5-ylene or 3-(methylaza)pent-1.5-ylene.

$R^{20}$ and $R^{21}$ together can be $C_4$–$C_5$-alkylene or oxaalkylene. In this case, they form, together with the N atom to which they are bonded, a saturated heterocyclic ring, for example a pyrrolidine, piperidine or morpholine ring.

(i) Compounds of the formula XIII

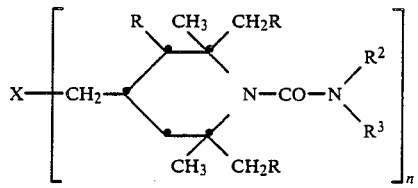

XIII in which n is 1 or 2 and, if n is 1, X is —CN, —$COOR^{24}$ or —$CHCOOR^{24}$, in which $R^{24}$ is $C_1$–$C_{18}$-alkyl, benzyl or cyclohexyl, or, if n is 2, X is —COO—$R^{25}$—OOC—, in which $R^{25}$ is $C_2$–$C_{12}$-alkylene, $C_4$–$C_{10}$-alkylene which is interrupted by —O— or —$N(C_1$–$C_4$-alkyl)—, or $C_6$–$C_{15}$-cycloalkylene, p-xylylene or hexahydroxylylene, and R, $R^2$ and $R^3$ are as defined above.

In this formula, $R^{24}$ can be a straight-chain or branched alkyl radical, for example methyl, butyl, n-octyl, tert.-octyl, 2-ethyloxyl, n-dodecyl or octadecyl. An alkylene or interrupted alkylene radical $R^{25}$ can be, for example, 1,2-ethylene, 1,2-propylene, tetramethylene, hexamethylene, octamethylene, 2,4,4-trimethylhexamethylene, 2,2-dimethylprop-1,3-ylene, 3-oxapent-1,5-ylene, 3,6-dioxaoct-1,8-ylene or 3-(methylaza)-pent-1,5-ylene. A cycloalkylene radical $R^{25}$ is, for example, 1,4-cyclohexylene, 4,4'-dicyclohexylene, 2,2-di(cyclohexylene)propane or decahydro-1,4-naphthylene.

(j) Oligomeric or polymeric compounds, the recurring molecular unit of which contains a group of the formula I.

These compounds can be, for example, polymers or copolymers of acrylates or acrylamides, methacrylates or methacrylamides, maleates or maleimides or vinyl esters or vinyl ethers which contain a group of the formula I. However, the polymer can also be a condensation polymer, for example a polyester, polyamide, polyurethane, polyurea, polyaminotriazine or polyether containing groups of the formula I in side chains. The groups of the formula I in the side chains can be bonded directly or via intermediate members to the main polymer chain.

In the case of copolymers, it is possible either for both monomers to contain a group of the formula I or for only one component to contain such a group.

Polymers of acrylates or methacrylates containing a group of the formula I and copolymers thereof with alkyl acrylates or alkyl methacrylates are preferred.

Those oligomeric or polymeric compounds having an average molecular weight not exceeding 20,000 are also preferred.

Of all the compounds of classes (a) to (j), those compounds containing a group of the formula I in which R is hydrogen are in each case preferred.

The process according to the invention consists of two reaction stages. In the first stage, the group of the formula Ia is converted into a group of the formula Ib, which is converted into the group of the formula I in the second stage:

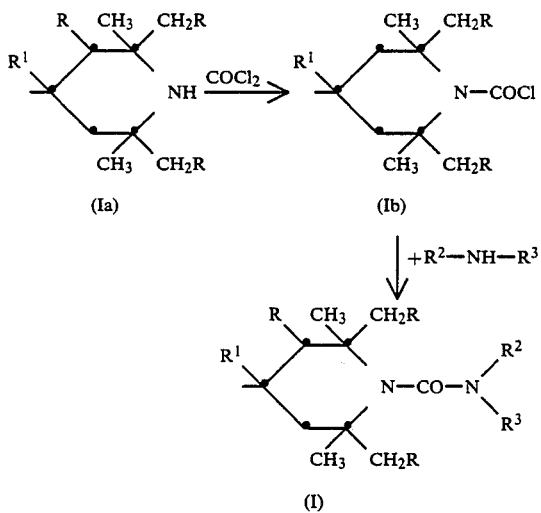

As already stated, the two reaction stages can be carried out as a one-pot process, i.e. the intermediate of the structure Ib does not have to be isolated.

Both stages are carried out in an inert solvent. Suitable solvents are hydrocarbons, for example benzene, toluene, xylene, cyclohexane or a mixture of alkanes; esters, for example methyl acetate, ethyl acetate or butyl acetate; and chlorinated solvents, for example methylene chloride, ethylene chloride or carbon tetrachloride. Those solvents in which all the educts and the N-carbamoyl compound are readily soluble but the base hydrochloride is insoluble are particularly advantageous. In such a case, the hydrochloride can be separated off in a simple manner by filtration.

Any proton acceptor can be used as the base, and organic amines are particularly suitable. An excess of the educts, i.e. an excess of the compound containing the group Ia in the first stage and an excess of the compound $R^2$—NH—$R^3$ in the second stage, can also be used as the base. However, a tertiary amine is preferably used as the auxiliary base, for example a trialkylamine, a dialkylaniline or a heterocyclic base.

In each case 1 molar equivalent of base is required for each of the two reaction stages. If an excess of the educt containing the group of the formula Ia is used in the first stage, about 0.5 molar equivalent of phosgene is added per molar equivalent of NH. However, if an auxiliary base is used, about 1 mol of phosgene and at least 1 mol of auxiliary base are added per molar equivalent of NH. Correspondingly, either at least 2 molar equivalents of $R^2NHR^3$ or 1 molar equivalent of $R^2NHR^3$ and at least 1 molar equivalent of the auxiliary base are added per molar equivalent of —COCl in the second reaction stage. A small excess of proton acceptor is generally advantageous.

Both reaction stages can be carried out at room temperature or slightly elevated or reduced temperature, preferably at temperatures below 40° C. The first reaction stage can already be carried out at surprisingly low temperatures, for example at $-30°$ to $+20°$ C.

The base hydrochloride formed can be filtered off after the first reaction stage. However, it is simpler to continue directly with the second reaction stage, without intermediate filtration, and to filter the mixture only after the second reaction stage. It is obvious to the expert that both reaction stages must be carried out with exclusion of moisture, and the same applies to any intermediate filtration.

The product is isolated as a distillation residue from the filtrate of the second reaction stage by distilling off the solvent, and, if necessary, can be purified by recrystallisation or another conventional method.

In the pure form, the 1-diorganocarbamoylpiperidines thus obtained are very stable compounds and can be used as stabilisers for organic materials, in particular against damage to these materials by the action of light. Such materials to be protected from light can be, for example, oils, fats, waxes, detergents or solvents, but the compounds which can be prepared according to the invention are particularly suitable as stabilisers for organic polymers. The following classes of polymers are examples of polymers which are sensitive towards the action of light and can be stabilised by addition of the compounds which can be prepared according to the invention:

1. Polymers of monoolefins and diolefins, for example polyethylene (which may be crosslinked), polypropylene, polyisobutylene, polybut-1-ene, polymethylpent-1-ene, polyisoprene and polybutadiene, and polymers of cycloolefins, for example of cyclopentene or norbornene.

2. Mixtures of the polymers mentioned under (1), for example mixtures of polypropylene with polyethylene or with polyisobutylene.

3. Copolymers of monoolefins and diolefins with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers and ethylene/acrylic acid copolymers and salts thereof (isomers), and terpolymers of ethylene with propylene and a diene, such as hexadiene, dicyclopentadiene or ethylidenenorbornene.

4. Polystyrene.

5. Copolymers of styrene or -methylstyrene with dienes or acrylic derivatives, for example styrene/butadiene, styrene/acrylonitrile, styrene/ethyl methacrylate, styrene/butadiene/ethyl acrylate and styrene/acrylintrile/methyl acrylate; high impact strength mixtures of styrene copolymers and another polymer, for example a polyacrylate, a diene polymer, or an ethylene/propylene/diene terpolymer; and block copolymers of styrene, for example styrene/butadiene/styrene, styrene/isoprene/styrene, styrene-ethylene/butylene-styrene and styrene-ethylene/propylene-styrene.

6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers listed under (5), for example those known as so-called ABS, MBS, ASA or AES polymers.

7. Halogen-containing polymers, for example polychloroprene, chlorinated rubber, chlorinated or chlorosulfonated polyethylene and epichlorohydrin homopolymers and copolymers, in particular polymers of halogen-containing vinyl compounds, for example polyvinyl chloride, polyvinylidene chloride, polyvinyl fluoride and polyvinylidene fluoride; and copolymers thereof, such as vinyl chloride/vinylidene chloride, vinyl chloride/vinyl acetate and vinylidene chloride/vinyl acetate.

8. Polymers which are derived from $\alpha,\beta$-unsaturated acids and derivatives thereof, such as polyacrylates, polymethacrylates, polyacrylamides and polyacrylonitriles.

9. Copolymers of the monomers listed under (8) with one another and with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers, methyl methacrylate/styrene copolymers and acrylonitrile/alkyl methacrylate/butadiene terpolymers.

10. Polymers which are derived from unsaturated alcohols and amines or their acyl derivatives or acetals, such as polyvinyl alcohol, polyvinyl acetae, stearate, benzoate or maleate, polyvinyl butyrate, polyallyl phthalate and polyallylmelamine.

11. Homopolymers and copolymers of cyclic ethers, such as polyalkylene glycols, polyethylene oxide, polypropylene oxide and copolymers thereof with bisglycidyl ethers.

12. Polyacetals, such as polyoxymethylene, and those polyoxymethylenes containing comonomers, for example ethylene oxide.

13. Polyphenylene oxides and sulfides and mixtures thereof with styrene polymers.

14. Polyurethanes which are derived from polyethers, polyesters and polybutadienes with terminal hydroxyl groups on the one hand and aliphatic or aromatic polyisocyanates on the other hand, and intermediates thereof (polyisocyanates, polyols and prepolymers).

15. Polyamides and copolyamides which are derived from diamines and dicarboxylic acids and/or aminocarboxylic acids or the corresponding lactams, such as polyamide 4, polyamide 6, polyamide 6/6, polyamide 6/10, polyamide 11, polyamide 12, poly-2,4,4-trimethylhexamethyleneterephthalamide and poly-m-phenyleneisophthalamide, and copolymers thereof with polyethers, for example with polyethylene glycol, polypropylene glycol and polytetramethylene glycol.

16. Polyureas, polyimides, polyamide-imides and polybenzimidazoles.

17. Polyesters which are derived from dicarboxylic acids and diols and/or hydroxycarboxylic acids or the corresponding lactones, such as polyethylene terephthalate, polybutylene terephthalate, poly-1,4-dimethylolcyclohexane terephthalate, ―[poly-2,2-bis-(4-hydroxyphenyl)-propane]terephthalate and polyhydroxybenzoates, and block polyether/esters which are derived from polyethers with terminal hydroxyl groups, dialcohols and dicarboxylic acids.

18. Polycarbonates.

19. Polysulfones and polyether-sulfones.

20. Crosslinked polymers which are derived from aldehydes on the one hand and phenols, urea and melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols, and vinyl compounds as crosslinking agents, as well as halogen-containing modifications thereof which are difficult to ignite.

23. Crosslinkable acrylic resins which are derived from substituted acrylates, for example from epoxy acrylates, urethane-acrylates or polyester-acrylates.

24. Alkyd resins, polyester resins and acrylate resins which are crosslinked with melamine resins, urea resins, polyisocyanates or epoxide resins.

25. Crosslinked epoxide resins which are derived from polyepoxides, for example from bis-glycidyl ethers or cycloaliphatic diepoxides.

26. Naturally occurring polymers, such as cellulose, natural rubber and gelatin, and their polymer-analogous chemically modified derivatives, such as cellulose acetates, propionates and butyrates, and the cellulose ethers, such as methylcellulose.

The stabilisers are added to the plastics in a concentration of 0.01 to 5% by weight, based on the material to be stabilised. Preferably, 0.03 to 1.5% by weight, and particularly preferably 0.2 to 0.6% by weight, of the compounds, based on the material to be stabilised, are incorporated into this material.

The incorporation can be effected during or after polymerisation, for example by mixing the compounds and, where appropriate, other additives into the melt by the conventional methods of the art, before or during shaping, or by applying the dissolved or dispersed compounds to the polymer, if necessary with subsequent evaporation of the solvent.

The compounds can also be added in the form of a master batch containing them in a concentration of, for example, 2.5 to 25% by weight to the plastics to be stabilised.

In addition to the compounds of the formula I, other known stabilisers can also be added to the plastics. These stabilisers can be, for example, antioxidants, light stabilisers or metal deactivators, or co-stabilisers, for example those of the phosphorous acid ester type. Other additives conventional in plastics technology, for example flameproofing agents, antistatic agents, plasticisers, lubricants, blowing agents, pigments, reinforcers or fillers, can also be added. The following compounds are specific examples of such known and conventional additives:

1. Antioxidants 1.1. Alkylated monophenols such as 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol and 2,6-di-tert.-butyl-4-methoxymethylphenol.

1.2. Alkylated hydroquinones, such as 2,6-di-tert.-butyl-4-methoxyphenol, 2,5-di-tert.-butyl-hydroquinone, 2,5-di-tert.-amyl-hydroquinone and 2,6-diphenyl-4-octadecyloxyphenol.

1.3. Hydroxylated thiodiphenyl ethers, such as 2,2'-thio-bis-(6-tert.-butyl-4-methylphenol), 2,2'-thio-bis-(4-octylphenol), 4,4'-thio-bis-(6-tert.-butyl-3-methylphenol) and 4,4'-thio-bis-(6-tert.-butyl-2-methylphenol).

1.4. Alkylidene-bisphenols, such as 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)-butane, 2,6-di-(3-tert.-butyl-5-methyl-2-hydroxybenzyl)-4-methylphenol, 1,1,3-tri-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)butyrate], di-(3-tert.-butyl-4-hydroxy-5-methylphenyl)-di-cyclopentadiene and di-[2-(3'-tert.-butyl-2'-hydroxy-5'-methyl-benzyl)-6-tert.-butyl-4-methyl-phenyl]terephthalate.

1.5. Benzyl compounds, such as 1,3,5-tri-(3,5-di-tert.-butyl-4-hydroxybenzyl)-2,4,6-trimethylbenzene, di-(3,5-di-tert.-butyl-4-hydroxybenzyl)sulfide, isooctyl 3,5-di-tert.-butyl-4-hydroxybenzyl-mercaptoacetate, bis-(4-tert.-butyl-3-hydroxy-2,6-dimethylbenzyl)dithiolterephthalate, 1,3,5-tris-(3,5-di-tert.-butyl-4-hydroxybenzyl)isocyanurate, 1,3,5-tris-(4-tert.-butyl-3-hydroxy-2,6-dimethylbenzyl)isocyanurate, dioctadecyl 3,5-di-tert.-butyl-4-hydroxybenzylphosphonate and the calcium salt of monoethyl 3,5-di-tert.-butyl-4-hydroxybenzyl-phosphonate.

1.6. Acylaminophenols, such as 4-hydroxy-lauric acid anilide, 4-hydroxy-stearic acid anilide and 2,4-bis-octylmercapto-6-(3,5-di-tert.-butyl-4-hydroxyanilino)-s-triazine.

1.7. Esters of β-(3,5-di-tert.-butyl-4-hydroxyphenol)-propionic acid with monohydric or polyhydric alcohols, for example with methanol, octadecanol, hexane-1,6-diol, neopentylglycol, diethylene thioglycol, diethylene glycol, triethylene glycol, pentaerythritol, tris-hydroxyethyl isocyanurate or di-hydroxyethyl-oxalic acid diamide.

1.8. Esters of β-(5-tert.-butyl-4-hydroxy-3-methylphenyl)propionic acid with monohydric or polyhydric alcohols, for example with methanol, octadecanol, hexane-1,6-diol, neopentylglycol, diethylene thioglycol, diethylene glycol, triethylene glycol, pentaerythritol, tris-hydroxyethyl isocyanurate or di-hydroxyethyl-oxalic acid diamide.

1.9. Amides of β-(3,5-di-tert.-butyl-4-hydroxyphenyl)-propionic acid, for example N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)-hydrazine. 2. UV Absorbers and light stabilisers 2.1. 2-(2'-Hydroxyphenyl)-benzotriazoles, for example the 5'-methyl, 3',5'-di-tert.-butyl, 5'-tert.-butyl, 5'-(1,1,1,3,3-tetramethylbutyl), 5-chloro-3',5'-di-tert.-butyl, 5-chloro-3'-tert.-butyl-5'-methyl, 3'-sec.-butyl-5'-tert.-butyl, 4'-octoxy and 3',5'-di-tert.-amyl derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted or unsubstituted benzoic acids, for example 4-tert.-butyl-phenyl salicylate, phenyl salicylate, octylphenyl salicylate, dibenzoylresorcinol, bis-(4-tert.-butylbenzoyl)-resorcinol, benzoylresorcinol and 2,4-di-tert.-butyl-phenyl 3,5-di-tert.-butyl-4-hydroxybenzoate.

2.4. Acrylates, for example ethyl or isooctyl α-cyano-β,β-diphenylacrylate, methyl α-carbomethoxy-cinnamate, methyl or butyl α-cyano-β-methyl-p-methoxy-cinnamate, methyl α-carbomethoxy-p-methoxy-cinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complex, with or without additional ligands, such as n-butylamine, triethanolamine or N-cyclohexyl-diethanolamine, nickel dibutyl-dithiocarbamate, nickel salts of monoalkyl, such as methyl or ethyl, 4-hydroxy-3,5-di-tert.-butyl-benzylphosphonates, nickel complexes of ketoximes, such as of 2-hydroxy-4-methyl-phenyl undecyl ketone oxime, and nickel complexes of 1-phenyl-4-lauroyl-5-hydroxypyrazole, with or without additional ligands.

2.6. Sterically hindered amines, for example bis-(2,2,6,6-tetramethylpiperidyl)sebacate, bis-(1,2,2,6,6-pentamethylpiperidyl)sebacate, bis-(1,2,2,6,6-pentamethylpiperidyl)n-butyl-3,5-di-tert.-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethyl-4-piperidyl)-hexamethylenediamine and 4-tert.-octylamino-2,6-dichloro-b 1,3,5-s-triazine, and tris-(2,2,6,6-tetramethyl-4-piperidyl)nitriloacetate.

2.7. Oxalic acid diamides, for example 4,4'-di-octyloxyoxanilide, 2,2'-dioctyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyloxanilide and its mixture with 2-ethoxy-2'-ethyl-5,4'-di-tert.-butyl-oxanilide, and mixtures of ortho- and para-methoxy- and of o- and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylidene-oxalic acid dihydrazide.

4. Phosphites and phosphonites, for example triphenyl phosphite, diphenyl alkyl phosphites, phenyl dialkyl phosphites, tri-(nonylphenyl)phosphite, trilauryl phosphite, trioctadecyl phosphite, distearyl pentaerythritol diphosphite, tris-(2,4-di-tert.-butylphenyl)phosphite, diisodecyl pentaerythritol diphosphite, di-(2,4-ditert.-butylphenyl)pentaerythritol diphosphite, tristearyl sorbitol triphosphite and tetrakis-(2,4-di-tert.-butylphenyl)-4,4'-biphenylene diphosphonite.

5. Compounds which destroy peroxide, for example esters of β-thio-dipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyl disulfide and pentaerythritol tetrakis-(β-dodecylmercapto)-propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes and alkali metal and alkaline earth metal salts of higher fatty acids, for example Ca stearate, Zn stearate, Mg stearate, Na ricinoleate, K palmitate, antimony pyrocatecholate and tin pyrocatecholate.

8. Nucleating agents, for example 4-tert.-butylbenzoic acid, adipic acid and diphenylacetic acid.

9. Fillers and reinforcers, for example calcium carbonates, silicates, glass fibres, asbestos, talc, kaolin, mica, barium sulfate, metal oxides and hydroxides, carbon black and graphite.

10. Other additives, for example plasticisers, lubricants, emulsifiers, pigments, fluorescent brighteners, flameproofing agents, antistatic agents and blowing agents.

The invention thus also relates to the organic polymers which have been stabilised by the addition of 0.01 to 5% by weight of a compound prepared according to the invention and which, where appropriate, may also contain other known and conventional additives. The plastics thus stabilised can be used in many diverse forms, for example as films, fibres, tapes or profiles, or as binders for varnishes, adhesives or putties.

The compounds prepared according to the invention can also be used as intermediates for the preparation of other polyalkylpiperidine derivatives which likewise have a light stabilising action. By reactions which do not modify the 1-diorganocarbamoyl group, it is possible to obtain compounds which cannot be prepared by direct phosgenation.

For example, a compound of the formula XIV can be converted by hydrolysis into a 1-carbamoyl-4-hydroxypiperidine XV, which is not readily accessible by direct phosgenation of 4-hydroxy-tetramethylpiperidine:

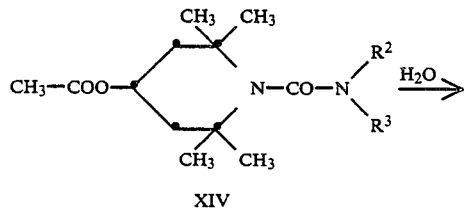

XIV

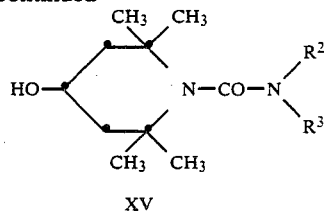

XV

Alternatively, XV can also be prepared by reducing the corresponding 4-oxo compound XVI:

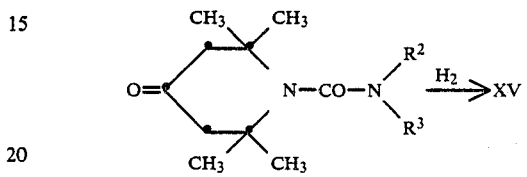

Reduction with complex borohydrides or catalytic hydrogenation is suitable in this case.

The 4-hydroxy compound XV can in turn be further reacted, for example by etherification, esterification or carbamoylation of the hydroxyl group.

Another example of transformation of compounds containing a group I is polymerisation or polycondensation with the formation of polymeric or oligomeric products. Although the resulting polymers, which contain a group I, can also be prepared from the corresponding polymers containing a group Ia by the phosgenation process described above, polymerisation of suitable monomers containing a group of the formula I can in many cases be the more advantageous route.

Overall, a large number of novel N-diorganocarbamoylpolyalkylpiperidines have become accessible by the carbamoylation process according to the invention and by transformation of the resulting products into corresponding secondary products.

These N-diorganocarbamoyl-polyalkylpiperidines belong, in particular, to the following classes of compounds:

(1) the compounds of the formula III listed above as group (a);

(2) the compounds of the formula IV listed above as group (b);

(3) the compounds of the formula V listed above as group (c); and those compounds of the formula V in which $R^3$ is hydrogen;

(4) the compounds of the formula VI

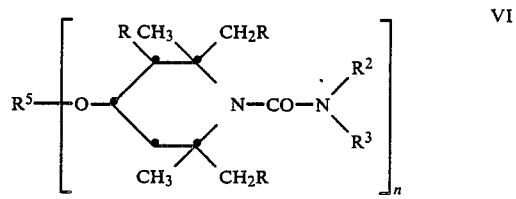

in which n is an integer from 1 to 4, and, if n is 1, $R^5$ is hydrogen, or, if n is 2, $R^5$ is $C_2$-$C_{12}$-alkylene, $C_4$-$C_{12}$-alkenylene, xylylene or a divalent acyl radical of an aliphatic or cycloaliphatic dicarboxylic acid, dicarbamic acid or phosphorus-containing acid, or, if n is 3, $R^5$ is a trivalent acyl radical of an aliphatic, cycloaliphatic, araliphatic, aromatic or heterocyclic tricarboxylic acid, tricarbamic acid or phosphorus-containing acid, or, if n is 4, $R^5$ is a tetravalent acyl radical of an aliphatic, cycloaliphatic or aromatic tetracarboxylic acid, and R, $R^2$ and $R^3$ are as defined above;

(5) compounds of the formula VII

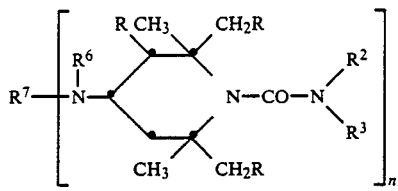

VII in which n is 1 or 2, $R^6$ is $C_1$-$C_{12}$-alkyl, $C_3$-$C_{12}$-alkoxyalkyl, $C_5$-$C_7$-cycloalkyl, $C_7$-$C_9$-aralkyl, $C_2$-$C_{18}$-alkanoyl, $C_3$-$C_5$-alkenoyl benzoyl, $C_2$-$C_{13}$-alkoxycarbonyl or $C_7$-$C_{11}$-aryloxycarbonyl and, if n is 1, $R^7$ is H, $C_1$-$C_{12}$-alkyl, $C_3$-$C_{12}$-alkoxyalkyl, $C_5$-$C_8$-cycloalkyl, $C_3$-$C_8$-alkenyl, glycidyl or cyanoethyl, or, if n if 2 $R^7$ is $C_2$-$C_{12}$-alkylene, $C_6$-$C_{15}$-arylene, xylylene or a —CH$_2$—CH(OH)—CH$_2$— or —CH—CH(OH)—CH—O—D—O—CH$_2$—CH(OH)—CH$_2$— group, in which D is $C_2$-$C_{10}$-alkylene, $C_6$-$C_{15}$-arylene or $C_6$-$C_{12}$-cycloalkylene, or, if $R^6$ is alkyl, cycloalkyl or aralkyl, $R^7$ can also be a divalent acyl radical of an aliphatic, cycloaliphatic or aromatic dicarboxylic acid or dicarbamic acid, or, if n is 1, $R^6$ and $R^7$, together with the N atom, are an imide radical of an aliphatic, cycloaliphatic or aromatic 1,2-dicarboxylic acid having 4 to 12 C atoms;

(6) compounds of the formula VIII

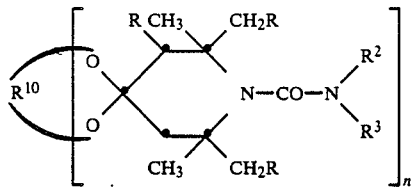

VIII in which n is 1 or 2, and, if n is 1, $R^{10}$ is $C_2$-$C_8$-alkylene or α-hydroxyalkylene or $C_4$-$C_{22}$-acyloxyalkylene, or, if n is 2, $R^{10}$ is the (—CH$_2$)$_2$C(CH$_2$—)$_2$ group, and R, $R^2$ and $R^3$ are as defined above;

(7) compounds of the formula IX,

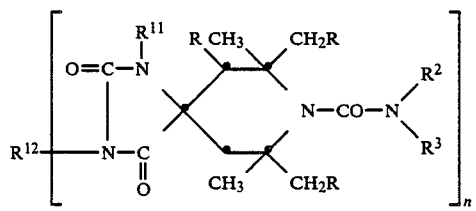

IX in which n is 1 or 2, $R^{11}$ is hydrogen, $C_1$-$C_{12}$-alkyl, allyl, benzyl, glycidyl or $C_2$-$C_6$-alkoxyalkyl, and, if n is 1, $R^{12}$ is hydrogen, $C_1$-$C_{12}$-alkyl, $C_3$-$C_5$-alkenyl, $C_7$-$C_9$-aralkyl, $C_5$-$C_8$-cycloalkyl, $C_2$-$C_4$-hydroxyalkyl, $C_3$-$C_6$-alkoxyalkyl, $C_6$-$C_{10}$-aryl or glycidyl, or, if n is 2, $R^{12}$ is $C_2$-$C_{12}$-alkylene, $C_6$-$C_{15}$-arylene, $C_4$-$C_8$-alkenylene or a —CH—CH(OH)—CH$_2$—O—D'O—CH$_2$—CH(OH)—CH$_2$— group, in which D is $C_2$-$C_{12}$-alkylene, $C_6$-$C_{15}$-arylene or $C_6$-$C_{12}$ cycloalkylene, and R, $R^2$ and $R^3$ are as defined above;

(8) compounds of the formula XII

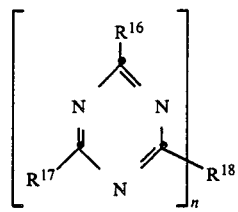

XII in which n is 1 or 2, $R^{16}$ is a group of the formula

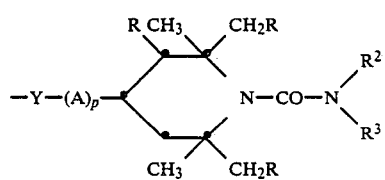

in which R, $R^2$ and $R^3$ are as defined above, Y is —O— or —NR$^{19}$—, $R^{19}$ is H, $C_1$-$C_{12}$-alkyl, $C_2$-$C_4$-hydroxyalkyl, $C_3$-$C_6$-alkoxyalkyl, cyclohexyl, benzyl or a group

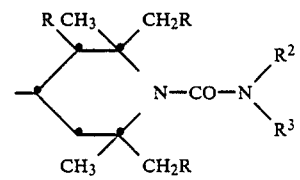

A is $C_2$-$C_6$-alkylene or —(CH$_2$)$_3$—O— and p is zero or 1, and $R^{17}$ has one of the meanings given for $R^{16}$ or is —NR$^{20}$R$^{21}$, —OR$^{22}$, —NHCH$_2$OR$^{23}$ or —N(CH$_2$OR$^{23}$)$_2$, in which $R^{20}$ has one of the meanings given for $R^{19}$ and $R^{21}$ is $C_1$-$C_{12}$-alkyl, cyclohexyl or benzyl, or $R^{20}$ and $R^{21}$ together are $C_4$-$C_5$-alkylene or oxaalkylene, $R^{22}$ is hydrogen, $C_1$-$C_{12}$-alkyl or phenyl and $R^{23}$ is hydrogen or $C_1$-$C_4$-alkyl, and, if n is 1, $R^{18}$ has one of the meanings given for $R^{16}$ and $R^{17}$, or, if n is 2, $R^{18}$ is a —Y—Q—Y— group, in which Q is $C_2$-$C_{12}$-alkylene, $C_4$-$C_{12}$-alkylene which is interrupted by —O—, —NH—, —N—alkyl or by a group of the formula

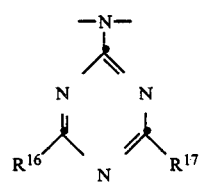

or Q is cyclohexylene, xylylene or phenylene;

(9) compounds of the formula XIII

XIII

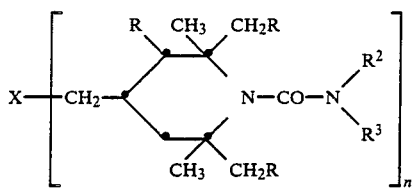

in which n is 1 or 2, and, if n is 1, X is —CN, —COOR$^{24}$, —CH$_2$NH$_2$, —CH$_2$OH or —CH$_2$COOR$^{24}$, in which R$^{24}$ is C$_1$-C$_{18}$-alkyl, benzyl or cycloalkyl, or, if n is 2, X is —CO—O—R$^{25}$—O—CO—, in which R$^{25}$ is C$_2$-C$_{12}$-alkylene, C$_4$-C$_{10}$-alkylene which is interrupted by —O— or —N(C$_1$C$_4$-alkyl)—, or C$_6$-C$_{15}$-cycloalkylene, p-xylylene or hexahydroxylylene, and R, R$^2$ and R$^3$ are as defined above; and

(10) oligomeric or polymeric compounds, the recurring molecular unit of which contains a group of the formula I, in particular those having an average molecular weight not exceeding 20,000, preferably those compounds which are polymers of acrylates or methacrylates containing a group of the formula I, or copolymers thereof with alkyl(meth)acrylates.

All these novel piperidine compounds can be used in the manner described above as stabilisers for organic materials, in particular as light stabilisers for organic polymers.

The examples which follow describe the process according to the invention and specific compounds thereby obtainable, as well as the conversion of such compounds into other compounds containing a group of the formula I by secondary reactions.

EXAMPLE 1

Carbamoylation in ethyl acetate

Example 1: A solution of 24.7 g (0.25 mol) of phosgene in about 150 ml of ethyl acetate is added dropwise to a solution of 99.7 g (0.5 mol) of 4-acetoxy-2,2,6,6-tetramethylpiperidine in 400 ml of ethyl acetate at 20°–22° in the course of 6 hours, with stirring. After the reaction mixture has been stirred for another 2 hours at room temperature, 63 ml (0.6 mol) of diethylamine are added dropwise in the course of about 30 minutes. The reaction mixture is stirred at room temperature for another 14 hours and is filtered and the salt residue is washed thoroughly with hexane. The combined filtrates are washed twice with water, three times with ice-cold N hydrochloric acid and again with water and dried over sodium sulfate and the solvent is distilled off in a vacuum rotary evaporator. The crude product is recrystallised from diisopropyl ether to give pure 1-diethylcarbamoyl-4-acetoxy-2,2,6,6-tetramethylpiperidine (Compound No. 1) of melting point 58°–60°.

Elementary analysis: C$_{16}$H$_{30}$N$_2$O$_3$ calculated: C 64.40, H 10.13, N 9.39%. (298.4) found: C 64.6, H 10.0, N 9.3%.

The $^1$H-NMR spectrum is in agreement with the given structure.

The N-carbamoyl-piperidines listed in Table 1 are prepared by a method analogous to that described in Example 1.

TABLE 1

| Compound No. | Name | Formula | Physical Data |
|---|---|---|---|
| 2 | 1-Dimethylcarbamoyl-2,2,6,6-tetramethylpiperidine | [structure with N—CO—N(CH$_3$)$_2$] | Melting point 69–70° |
| 3 | 1-Diethylcarbamoyl-2,2,6,6-tetramethylpiperidine | [structure with N—CO—N(C$_2$H$_5$)$_2$] | Melting point 32–34° |
| 4 | 1-Diethylcarbamoyl-2,2,6,6-tetramethyl-4-benzoyloxypiperidine | [structure with phenyl-COO- and N—CO—N(C$_2$H$_5$)$_2$] | Melting point 44–46° |
| 5 | 1-Diethylcarbamoyl-2,2,6,6-tetramethylpiperid-4-one | [structure with O= and N—CO—N(C$_2$H$_5$)$_2$] | Melting point 80–82° |

TABLE 1-continued

| Compound No. | Name | Formula | Physical Data |
|---|---|---|---|
| 6 | 1-Di-(2-hydroxyethyl)-carbamoyl-2,2,6,6-tetramethylpiperidine | [piperidine ring with 4 CH$_3$ groups]–N—CO—N(CH$_2$CH$_2$OH)$_2$ | oil |
| 7 | 3-Ethyl-3-acetoxymethyl-8,8,10,10-tetramethyl-9-diethylcarbamoyl-1,5-dioxa-9-azo-spiro[5.5]decane | CH$_3$COOCH$_2$–C(C$_2$H$_5$)(–O–)$_2$–[piperidine with 4 CH$_3$]–N—CO—N(C$_2$H$_5$)$_2$ | Melting point 80–81° |
| 8 | N,N'—dimethyl-N,N'—bis-tetramethylpiperidinecarbonyl)-ethylenediamine | | m.p. 234–236° |
| 9 | 8-morpholinocarbonyl-1,3,8-triaza-2,4-dioxo-3-docdecyl-7,7,9,9-tetramethylspiro[4.5]-decane | | m.p. 152–153° |
| 10 | 1-piperidinocarbonyl-4-(β-piperidinopropionoxy)-2,2,6,6-tetramethylpiperidine | | m.p. 84–86° |

EXAMPLE 2

Carbamoylation in toluene

To a solution of phosgene in toluene (24.7 ml of a 20% solution, corresponding to 0.05 mol of phosgene) is added dropwise at −30°, within one hour, the solution of 14.2 g (0.1 mol) of 2,2,6,6-tetramethylpiperidine in 25 ml of toluene. Stirring is maintained at 0° for a further 2 hours; there are then added dropwise, within 2 hours, 26.7 g (0.11 mol) of di-n-octylamine in 25 ml of toluene, and the mixture is subsequently stirred for 16 hours at room temperature. In further processing, the salt which has precipitated is filtered off; the filtrate is afterwards repeatedly washed with a small amount of water, dried over sodium sulfate, and the solvent is completely distilled off in a water-jet vacuum. The crude compound is further purified by column chromatography on silica gel (eluant: hexane/diethyl ether 9:1) to obtain the pure 1-di-n-octylcarbamoyl-2,2,6,6-tetramethylpiperidine (compound No. 11) as a viscous liquid; n$_D^{20}$: 1.4728.

The $^1$H-NMR spectrum of the resulting compound is in agreement with the given structure.

Elementary analysis:

C$_{26}$H$_{52}$N$_2$O calculated: C 76.41, H 12.83, N 6.85%. (408.7) found: C 76.5, H 12.6, N 6.8%.

EXAMPLE 3

Carbamoylation with the addition of an auxiliary base

The solution of 39.6 g (0.4 mol) of phosgene in about 300 ml of ethyl acetate is added dropwise at 0°–5° C. within about 6 hours, with stirring, to a solution of 84.5 g (0.4 mol) of 4-acryloyloxy-2,2,6,6-tetramethylpiperidine, 0.2 g of di-tert-butyl-p-cresol and 129.3 g (1.0 mol) of diisopropylethylamine in 300 ml of ethyl acetate. After a further 3 hours' stirring at room temperature, there is added dropwise to the white suspension at about 20°, in the course of one hour (with slight external cooling and vigorous stirring), a solution of 35.7 g (0.41 mol) of morpholine in 40 ml of ethyl acetate. The reaction mixture is stirred for a further 6 hours at room temperature, and is then filtered; the salt residue is well washed with hexane, and the filtrate is freed, in a vacuum rotary evaporator, from the solvents and the unreacted diisopropylethylamine. The residue is dissolved in methylene chloride, and this solution is washed twice with water, three times with cold N hydrochloric acid and again twice with water; the organic phase is subsequently dried over sodium sulfate, and the solvent is distilled off in vacuo. The crude product, solidifying in crystalline form, is recrystallised in diisopropyl ether to thus obtain pure 1-morpholinocarbonyl-4-acryloyloxy-2,2,6,6-tetramethylpiperidine, m.p. 129°–130° (compound No. 12).

Elementary analysis: C$_{17}$H$_{28}$N$_2$O$_4$ calculated: C 62.94; H 8.70, N 8.64%. (324.4) found: C 63.2, H 8.8, N 8.4%.

The $^1$NMR spectrum is in agreement with the given structure.

1-Piperidonocarbonyl-4-acryloyloxy-2,2,6,6-tetramethylpiperidine, m.p. 90°–92° (compound No. 13) is produced in an analogous manner.

EXAMPLE 4

Hydrolysis to 4-hydroxypiperidine

A solution of 5.7 g of sodium hydroxide in 50 ml of methanol is added to a solution of 41.8 g of 1-diethylcarbamoyl-4-acetoxy-2,2,6,6-tetramethylpiperidine [0.14 mol (compound No. 1)] in 200 ml of methanol. The reaction mixture is stirred for 16 hours at room temperature, and is then freed from methanol in the vacuum rotary evaporator; the residue is subsequently dissolved in methylene chloride, and washed three times with water. The organic phase is dried over sodium sulfate; it is afterwards filtered, and the methylene chloride is distilled off. The crystalline residue is recrystallised in diisopropyl ether to thus obtain pure 1-diethylcarbamoyl-4-hydroxy-2,2,6,6-tetramethylpiperidine (compound No. 14), m.p. 118°–119°.

Elementary analysis: $C_{14}H_{28}N_2O_2$ calculated: C 65.59, H 11.01, N 10.93%. (256.4) found: C 65.6, N 10.8, N 11.0%.

The $^1$H-NMR spectrum is in agreement with the given structure of the compound obtained.

There is obtained in an analogous manner by hydrolysis of the compound No. 9: 1-morpholinocarbonyl-4-hydroxy-2,2,6,6-tetramethylpiperidine, m.p. 142°-143° (compound No. 15); and by hydrolysis of the compound No. 10: 1-piperidinocarbonyl-4-hydroxy-2,2,6,6-tetramethylpiperidine (compound No. 16).

EXAMPLE 5

Reaction of 4-hydroxypiperidines

To a solution of 15.4 g of 1-diethylcarbamoyl-4-hydroxy-2,2,6,6-tetramethylpiperidine (0.06 mol) (compound No. 14) and 6.9 g (0.03 mol) of dimethyl sebacate in 200 ml of xylene is added 0.1 ml of tetrabutyl orthotitanate, and the mixture is slowly heated, in a gently stream of nitrogen, to a maximum temperature of 145°, the methanol formed being continuously distilled off, and finally also the xylene being completely distilled off slowly in the course of 8 hours. After cooling, the reaction mixture is dissolved in methylene chloride; the solution is then washed with water, dried over sodium sulfate, and the solvent is subsequently distilled off. The crude compound, solidifying in crystalline form, is recrystallized from pentane to thus obtain pure bis-(1-diethylcarbamoyl-2,2,6,6-tetramethylpiperidin-4-yl)sebacate (compound No. 17), m.p. 72°-73°.

Elementary analysis: $C_{38}H_{70}N_4O_6$ calculated: C 67.22, H 10.39, N 8.25%. (679.0) formed: C 67.0 H 10.5 N 8.1%.

The $^1$NMR spectrum of the compound obtained is well compatible with the given structure.

There is obtained in an analogous manner by reaction of the compound No. 14 with dimethyl adipate: bis-(1-diethylcarbamoyl-2,2,6,6-tetramethylpiperidin-4-yl)adipate, m.p. 104°-105° (compound No. 18).

By an analogous reaction of the compound No. 16 with an excess of diethyl carbonate and subsequently with hexanediol-1,6 in the molar ratio of 2:1, there is obtained hexamethylene-bis(1-piperidinocarbonyl-2,2,6,6-tetramethylpiperidin-4-yl)carbonate (compound No. 19), m.p. 128°-130°.

Reaction of the compound No. 15 with hexamethylenediisocyanate yields O,O'-bis(1-morpholinocarbonyl-2,2,6,6-tetramethyl-4-piperidinyl)-N,N'-hexamethylene dicarbonate (compound No. 20), which melts at 128°-130° and at 202°-204°.

EXAMPLE 6

Polymerisation

A solution of 40 mg of azobisisobutyronitrile in 5 ml of benzene is added in the course of 5 minutes, with stirring, to a solution, heated to 78°, of 11.4 g (0.035 mol) of 1-morpholinocarbonyl-4-acryloyloxy-2,2,6,6-tetramethylpiperidine (compound No. 12) in 45 ml of benzene. The radical polymerisation is subsequently continued at 78° for 7 hours. After about 35 ml of benzene have been distilled off in vacuo, the polymer concentrate is slowly poured at room temperature, with vigorous stirring, into 200 ml of diethyl ether, as a result of which the polymer precipitates as white powder. The precipitate is filtered off, carefully washed with diethyl ether, and dried at 60° in vacuo. The colourless pulverulent poly-1-morpholinocarbonyl-4-acryloyloxy-2,2,6,6-tetramethylpiperidine thus obtained has a softening point ($T_s$) of 185°-190° and a mean molecular weight ($\overline{M}_n$) of 3400 (compound No. 21).

There is obtained in an analogous manner, by polymerisation of the compound No. 13: poly-1-piperidinocarbonyl-4-acryloyloxy-2,2,6,6-tetramethylpiperidine (compound No. 22), which softens at 160° and has an $\overline{M}_n$ of 3200.

EXAMPLE 7

Stabilisation of polypropylene sheets 100 parts of polypropylene powder (Moplen, fibre grade, from Montedison) are homogenised with 0.2 part of octadecyl β-(3,5-di-tert.butyl-4-hydroxyphenyl)-propionate and 0.25 part of a light stabiliser from the following Table 2 at 200° for 10 minutes in a Brabender plastograph. The mixture thus obtained is removed as rapidly as possible from the kneader, and is then pressed in a toggle press to give a sheet 2-3 mm in thickness. A part of the pressed sheet obtained is cut out and subsequently compressed between two high-gloss hard aluminium sheets in a hydraulic laboratory press for 6 minutes at 260°, under a pressure of of 12 tons, to obtain a 0.1 mm thick sheet; this sheet is tempered at 150° for 1 hour, and is then immediately quenched in cold water. Sections are stamped out from the sheet material and are exposed in a Xenotest 1200. These test specimens are taken from the exposure apparatus at regular intervals of time, and are tested in an IR spectrophotometer for their carbonyl content. The increase in the carbonyl extinction at 5.85 μm during exposure is a measure for the photo-oxidative degradation of the polymer (cp. L Balaban et al., J. Polymer Sci, Part C, 22, 1059-1071 (1969)), and, as experience shows, is associated with a deterioration of the mechanical properties of the polymer. The time until a carbonyl extinction of about 0.3 is reached, at which point the sheet is brittle, is taken as a measure of the protective action.

TABLE 2

| Light stabiliser | Exposure time up to a carbonyl extinction of 0.3 |
| --- | --- |
| none | 890 h |
| compound No. 8 | 2385 h |
| compound No. 9 | >3360 h |
| compound No. 10 | >3200 h |
| compound No. 17 | 6080 h |
| compound No. 18 | >5540 h |
| compound No. 20 | >3400 h |
| compound No. 21 | 2170 h |
| compound No. 22 | 2080 h |

EXAMPLE 8

Stabilisation of a 2-layer metal-effect lacquer

Aluminium sheets 0.5 mm in thickness are coated with an aluminium-pigmented priming lacquer based on polyester/cellulose acetobutyrate/melamine resin. Onto the wet priming lacquer is then sprayed a clear lacquer of the following composition:

- 58.3 parts of Viacryl®VC 373 (acrylic resin, Vianova Vienna),
- 27.3 parts of Maprenyl®MF 590 (melamine resin, Höchst AG, Frankfurt),
- 1.0 part of a 1% solution of a silicone resin in xylene,
- 4.0 parts of Solvesso®150 (aromatic solvent mixture),
- 5.4 parts of xylene, and
- 4.0 parts of ethyl glycol acetate.

To this is added in each case 0.9 part of one of the light stabilisers given in Table 3. This clear lacquer has a viscosity of 21 sec/DIN cup 4. It is applied in a layer thickness of 40 μm, and is stoved at 130° for 39 minutes.

The specimens are exposed to weathering in a UVCON accelerated weatherometer (Atlas) having a cycle of 4 hours of UV irradiation at 60° and 4 hours of weathering at 50° for 2000 hours. Then 20°-gloss, according to DIN 67530, is measured after 1000 hours and after 2000 hours. In addition, the specimens are examined at regular intervals of time, under a stereomicroscope, to determine whether or not crack formation has occurred. The results are summarised in Table 3.

TABLE 3

| Light stabiliser | 20°-Gloss after | | | Crack formation perceptible |
| --- | --- | --- | --- | --- |
| | 0 h | 1000 h | 2000 h | |
| none | 97 | 47 | 9 | after 1600 h |
| compound No. 7 | 92 | 75 | 54 | none |
| compound No. 8 | 96 | 64 | 36 | none |
| compound No. 17 | 94 | 78 | 63 | none |

TABLE 3-continued

| Light stabiliser | 20°-Gloss after | | | Crack formation perceptible |
| --- | --- | --- | --- | --- |
| | 0 h | 1000 h | 2000 h | |
| compound No. 18 | 89 | 59 | 57 | none |

What is claimed is:

1. A compound of the formula VI

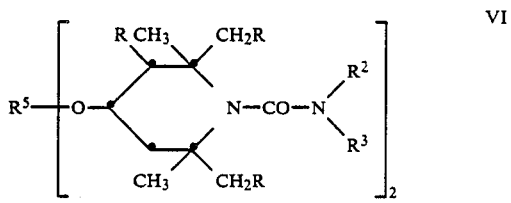

wherein R is hydrogen; $R^2$ and $R^3$ independently are $C_1$-$C_{18}$-alkyl; or $R^2$ and $R^3$, together with the N atom to which they are bonded, form a piperidine, pyrrolidine, morpholine, or 4-alkylpiperidine ring; and $R^5$ is a divalent acyl radical of an aliphatic or cycloaliphatic dicarboxylic acid.

* * * * *